(12) United States Patent
Yamamoto

(10) Patent No.: US 10,381,230 B2
(45) Date of Patent: Aug. 13, 2019

(54) GALLIUM NITRIDE SUBSTRATE AND OPTICAL DEVICE USING THE SAME

(71) Applicant: SCIOCS Company Limited, Hitachi-shi (JP)

(72) Inventor: Shunsuke Yamamoto, Tokyo (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 443 days.

(21) Appl. No.: 15/012,459

(22) Filed: Feb. 1, 2016

(65) Prior Publication Data

US 2016/0148817 A1 May 26, 2016

Related U.S. Application Data

(62) Division of application No. 13/781,568, filed on Feb. 28, 2013, now abandoned.

(30) Foreign Application Priority Data

Mar. 2, 2012 (JP) .................... 2012-047203

(51) Int. Cl.
*H01S 5/02* (2006.01)
*C01B 21/06* (2006.01)
(Continued)

(52) U.S. Cl.
CPC .... *H01L 21/30625* (2013.01); *C01B 21/0632* (2013.01); *C30B 25/00* (2013.01);
(Continued)

(58) Field of Classification Search
None
See application file for complete search history.

(56) References Cited

U.S. PATENT DOCUMENTS 6,447,604 B1 * 9/2002 Flynn ..................... C30B 25/00
117/89
6,667,184 B2 12/2003 Motoki et al.
(Continued)

FOREIGN PATENT DOCUMENTS

CN 101570004 A 11/2009
JP 2001-322899 A 11/2001
(Continued)

OTHER PUBLICATIONS

Japanese Office Action dated Jun. 7, 2016 with a partial English translation.
(Continued)

*Primary Examiner* — Melvin C. Mayes
*Assistant Examiner* — Michael Forrest
(74) *Attorney, Agent, or Firm* — McGinn IP Law Group, PLLC

(57) ABSTRACT

A method of processing a gallium nitride substrate, includes providing a gallium nitride substrate, polishing a surface of the gallium nitride substrate, and cleaning the polished surface of the gallium nitride substrate. The polished surface includes a GaLα/CKα peak intensity ratio in energy dispersive X-ray microanalysis (EDX) spectrum which is not less than 2, the EDX spectrum being obtained in an EDX of the surface of the gallium nitride substrate using a scanning electron microscope (SEM) at an accelerating voltage of 3 kV.

4 Claims, 2 Drawing Sheets

(51) Int. Cl.

| | |
|---|---|
| *C30B 29/40* | (2006.01) |
| *H01L 21/02* | (2006.01) |
| *H01L 29/20* | (2006.01) |
| *H01L 33/00* | (2010.01) |
| *H01L 33/22* | (2010.01) |
| *G01N 23/2252* | (2018.01) |
| *C30B 25/00* | (2006.01) |
| *H01S 5/323* | (2006.01) |
| *H01L 21/306* | (2006.01) |
| *H01L 21/66* | (2006.01) |
| *H01L 33/32* | (2010.01) |

(52) U.S. Cl.
CPC ....... *C30B 29/406* (2013.01); *G01N 23/2252* (2013.01); *H01L 21/02057* (2013.01); *H01L 21/30612* (2013.01); *H01L 22/12* (2013.01); *H01L 29/2003* (2013.01); *H01L 33/0075* (2013.01); *H01S 5/0206* (2013.01); *H01S 5/32341* (2013.01); *H01L 33/32* (2013.01)

(56) References Cited

U.S. PATENT DOCUMENTS

| | | | |
|---|---|---|---|
| 7,112,826 B2 | 9/2006 | Motoki et al. | |
| 7,569,493 B2* | 8/2009 | Hachigo | ........... H01L 21/02052 |
| | | | 257/615 |
| 7,919,343 B2 | 4/2011 | Ishibashi et al. | |
| 2003/0080345 A1 | 5/2003 | Motoki et al. | |
| 2008/0176400 A1 | 7/2008 | Hachigo et al. | |
| 2009/0273060 A1 | 11/2009 | Ishibashi et al. | |
| 2010/0009483 A1* | 1/2010 | Jiang | ................... H01L 33/22 |
| | | | 438/39 |
| 2010/0200865 A1* | 8/2010 | Fujito | ................... C30B 29/403 |
| | | | 257/76 |
| 2011/0146565 A1 | 6/2011 | Ishibashi et al. | |

FOREIGN PATENT DOCUMENTS

| | | |
|---|---|---|
| JP | 2003-165799 A | 6/2003 |
| JP | 2004-269313 A | 9/2004 |
| JP | 2009-272380 A | 11/2009 |

OTHER PUBLICATIONS

Chinese Office Action dated Jul. 15, 2016, with an English translation.
Chinese Office Action dated Mar. 10, 2017, with an English translation.
Japanese Office Action dated Dec. 3, 2014 with an English translation.
Aida, et al. "Chemical Mechanical Polishing of Gallium Nitride with Colloidal Silica", Journal of the Electrochemical Society, 158(12), pp. H1206-H1212, Nov. 2011.

* cited by examiner

GALLIUM NITRIDE SUBSTRATE AND OPTICAL DEVICE USING THE SAME

RELATED APPLICATIONS

The present Application is a divisional Application of U.S. patent application Ser. No. 13/781,568 which was filed on Feb. 28, 2013 now abandoned, which is based on Japanese patent application No. 2012-047203 filed on Mar. 2, 2012, the entire contents of which are incorporated herein by reference.

BACKGROUND OF THE INVENTION

1. Field of the Invention

The invention relates to a gallium nitride substrate and an optical device using the gallium nitride substrate.

2. Description of the Related Art

GaN-based semiconductor crystals such as gallium nitride (GaN) has attracted attention as a material of optical devices such as light emitting diode (LED) which emits high-intensity blue light or long-life laser diode (LD) which emits blue light.

Bulk crystal growth of the GaN-based semiconductor crystals is difficult, and accordingly, it is difficult to produce a large single crystal GaN with high quality. However, in recent years, a method of manufacturing a GaN-based semiconductor crystal has been proposed, using a DEEP (Dislocation Elimination by the Epi-growth with Inverted-Pyramidal Pits) method or a VAS (Void-Assisted Separation) method, etc., and also using GaN free-standing substrate in which a GaN single crystal is grown on a heterogeneous substrate by a HVPE (Hydride Vapor Phase Epitaxy) method.

In the DEEP method, a patterned mask of SiN, etc., is formed on a GaAs substrate which is removable by etching, a GaN layer is the formed thereon, plural pits surrounded by facet planes are intentionally formed on a crystal surface and dislocations are accumulated at a bottom of the pits to reduce dislocation in other regions. The GaAs substrate is then removed, thereby obtaining a GaN free-standing substrate with reduced dislocation (see, e.g., JP-A-2003-165799).

In the VAS method, a GaN layer is grown on a substrate of sapphire, etc., via a GaN substrate with voids and a TiN thin film having a mesh structure, thereby allowing separation of the GaN substrate and reduction of dislocation at the same time (see, e.g., JP-A-2004-269313).

The GaN free-standing substrate obtained by the above-mentioned methods is flattened by grinding and polishing front and back surfaces of a substrate epitaxially grown by the HVPE method. Subsequently, an outer periphery of the substrate is shaped in order to have a circular shape with a given diameter. Then, after removing processing strain by wet-etching, etc., the substrate is cleaned and a GaN mirror wafer is thus obtained.

A known method of polishing the GaN substrate is, e.g., disclosed in JP-A-2001-322899. In JP-A-2001-322899, after the GaN substrate is fixed to a substrate-attaching board using a wax, both front and back surfaces of the GaN substrate are polished by loose abrasive supplied onto the surface plate. Diamond is used as the loose abrasive by taking into consideration hardness of the GaN substrate.

SUMMARY OF THE INVENTION

However, crystal quality of an epitaxial growth layer is poor is case of epitaxial growth using the GaN substrate polished by the method of JP-A-2001-322899 and an optical device using such a substrate has a problem that emission intensity decreases, which causes failure and a decrease in a yield. As a result of intensive examination of this problem, it was found that the diamond used as the loose abrasive is embedded into and remains on the surface of the GaN substrate when the GaN substrate is polished and crystal quality of the epitaxial growth layer deteriorates due to a carbon component of the diamond. It is also found that the wax used when polishing remains and the crystal quality deteriorates due to a carbon component of the wax.

Accordingly, it is an object of the invention to provide a gallium nitride substrate that an amount of residual carbon on a substrate surface is small. It is another object of the invention to provide an optical device that is formed using the gallium nitride substrate and has excellent emission intensity.

(1) According to one embodiment of the invention, a gallium nitride substrate wherein a GaLα/CKα peak intensity ratio in EDX spectrum is not less than 2, the EDX spectrum being obtained in energy dispersive X-ray microanalysis (EDX) of a surface of the gallium nitride substrate using a scanning electron microscope (SEM) at an accelerating voltage of 3 kV.

In the above embodiment (1) of the invention, the following modifications and changes can be made.

(i) The GaLα/CKα peak intensity ratio in the EDX spectrum is not less than 3.

(2) According to another embodiment of the invention, an optical device comprises:

a device structure formed on the gallium nitride substrate according to the embodiment (1).

In the above embodiment (2) of the invention, the following modifications and changes can be made.

(ii) The GaLα/CKα peak intensity ratio in the EDX spectrum is not less than 3.

Points of the Invention

According to one embodiment of the invention, a gallium nitride (GaN) substrate is constructed so as to satisfy the GaLα/CKα peak intensity ratio of not less than 2. Based on the GaLα/CKα peak intensity ratio which is calculated as an amount of C (carbon) with respect to Ga, an increase or decrease in the amount of residual carbon can be determined so as to evaluate the amount of residual carbon on the surface of the GaN substrate. By satisfying the above GaLα/CKα peak intensity ratio, it is possible to obtain the gallium nitride substrate with the reduced amount of residual carbon on the surface thereof. Thus, the crystalline quality of an epitaxial layer grown on the gallium nitride substrate can be enhanced.

BRIEF DESCRIPTION OF THE DRAWINGS

Next, the present invention will be explained in more detail in conjunction with appended drawings, wherein.

DETAILED DESCRIPTION OF THE PREFERRED EMBODIMENTS

When a GaN substrate is polished, carbon derived from diamond or wax remains on the substrate surface, as described above. The residual carbon deteriorates crystal quality of an epitaxial growth layer to be epitaxially grown. Therefore, the present inventors measured an amount of residual carbon on a substrate surface and intensively examined a relation between the amount of carbon and a decrease in emission intensity of an optical device to be formed. In detail, the surface of the GaN substrate was measured in energy dispersive X-ray microanalysis (EDX) and an amount of carbon was calculated from a GaLα/CKα peak intensity ratio in the obtained EDX spectrum. Then, influence of the amount of carbon on an increase or decrease in emission intensity was evaluated. As a result, it was found that, when the GaLα/CKα peak intensity ratio is greater than a predetermined value and the amount of residual carbon near the surface the GaN substrate decreases, good crystal quality of the epitaxial growth layer is obtained and also the emission intensity of the optical device can be improved, and the invention was made based on the findings.

GaN Substrate

When a surface of a gallium nitride substrate (GaN substrate) in the present embodiment is measured by a scanning electron microscope (SEM) at an accelerating voltage of 3 kV in energy dispersive X-ray microanalysis (EDX), a GaLα/CKα peak intensity ratio in EDX spectrum obtained by the EDX is not less than 2.

Figure 1:
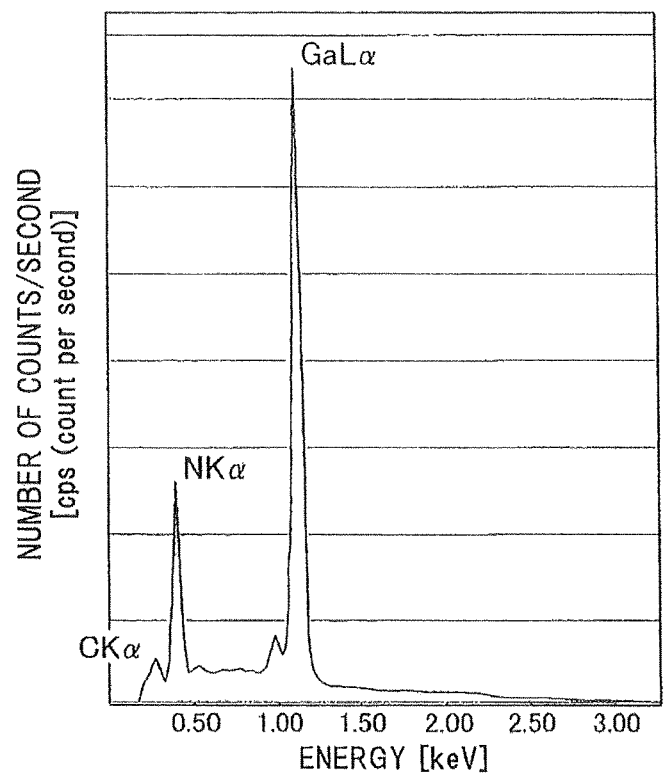
FIG. 1 is a diagram illustrating EDX spectrum of a GaN substrate at an accelerating voltage of 3 kV.

The SEM is a device for observing a surface profile of a sample by irradiating an electron beam, which is a focused electron beam (electron) emitted from an electron source (electron gun), and scanning the surface of the sample to detect secondary electrons emitted from the surface of the sample. In the EDX, a characteristic X-ray generated from the surface of the sample at the time of the electron-beam-scanning by the SEM is measured to identify elements contained on the surface of the sample. In addition, the number of counts/second (peak intensity) of the characteristic X-ray with given energy is measured to evaluate the content of a specific element. The EDX spectrum obtained by the EDX is as shown in, e.g., FIG. 1 (EDX spectrum of a GaN substrate in below-described Examples at an accelerating voltage of 3 kV). In FIG. 1, the horizontal axis indicates energy of the characteristic X-ray and the vertical axis indicates the number of counts/second [cps (count per second)] of the characteristic X-ray at such energy. From FIG. 1, an approximate content of an element constituting the GaN substrate is understood from a level of peak (peak intensity). In the present embodiment, in order to evaluate the amount of residual carbon on the surface of the GaN substrate, an increase or decrease in the amount of residual carbon is determined based on a GaLα/CKα peak intensity ratio which is calculated as an amount of C (carbon) with respect to Ga. Here, in the GaN substrate of the present embodiment, the GaLα/CKα peak intensity ratio is not less than 2, which indicates that C with respect to Ga is not more than a predetermined ratio.

Meanwhile, in the SEM, the electron beam (electron) is focused at a predetermined accelerating voltage. Here, the electron penetrates deeper from the sample surface when the accelerating voltage is higher and this allows information about a deeper region from the sample surface to be obtained. In other words, in the SEM, it is possible to obtain information about a region at a predetermined depth from the sample surface by adjusting the accelerating voltage to control electron penetration depth.

Here, a relation between an accelerating voltage of the SEM and a depth of the sample (GaN substrate) to be measured will be described. The electron penetration depth depends on an accelerating voltage of irradiated electron and an atomic weight, atomic number and density of a measurement sample, and is calculated from the following formula (1) (see, e.g., JPn. J. ApPl. Phys. Vol. 40 (2001) PP. 476-479).

$$\mathrm{Re} = \frac{0.0276A}{\rho Z^{0.889}} E_b^{1.67} (\mu m) \qquad (1)$$

Figure 2:
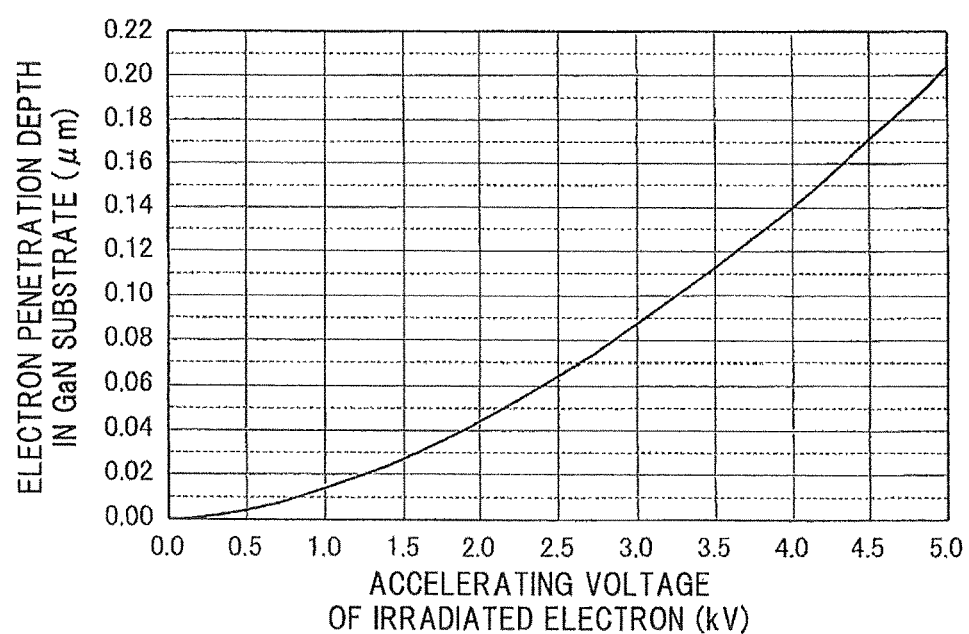
FIG. 2 is a diagram illustrating a correlative relationship between an accelerating voltage (Eb) and electron penetration depth (Re)

FIG. 2 shows a correlative relationship between an accelerating voltage (Eb) and electron penetration depth (Re) in the above formula (1) in case that a GaN substrate is measured. FIG. 2 shows that the electron penetration depth increases with an increase in the accelerating voltage. In other words, the electron penetration depth is smaller (shallower) when the accelerating voltage is lower and this allows information about a region closer to the sample surface to be obtained. For example, Re is 0.09 μm when Eb is 3 kV, and Re is 0.20 μm when Eb is 5 kV.

It is preferable to scan at a low accelerating voltage in the present embodiment since the amount of carbon on the surface of the GaN substrate is evaluated. In this regard, however, when the accelerating voltage is low, the number of detectable characteristic X-rays of elements decreases and also intensity of the characteristic X-ray to be detected is low, which results in that it takes very long time to measure. Therefore, in the present embodiment, the amount of carbon on the surface of the GaN substrate is evaluated by EDX using the SEM at an accelerating voltage of 3 kV.

In the gallium nitride substrate of the present embodiment, the GaLα/CKα peak intensity ratio in the EDX spectrum is not less than 2 in energy dispersive X-ray microanalysis (EDX) using the SEM at an accelerating voltage of 3 kV. By this configuration, it is possible to obtain the gallium nitride substrate in which the amount of residual carbon on the surface thereof is small. Therefore, in case of crystal growth using this gallium nitride substrate as abase substrate, crystal quality of the epitaxial growth layer to be obtained can be improved.

In the above-mentioned gallium nitride substrate, the GaLα/CKα peak intensity ratio in the EDX spectrum is preferably not less than 3. By such a configuration, it is possible to further reduce the amount of residual carbon on the surface of the gallium nitride substrate and it is thus possible to further improve the crystal quality of the epitaxial growth layer.

In an optical device formed using the gallium nitride substrate of the present embodiment, since the crystal quality of the epitaxial growth layer to be crystal-grown is good, emission intensity is high.

Method of Manufacturing Gallium Nitride Substrate

A method of manufacturing such a gallium nitride substrate includes a step of forming a gallium nitride substrate (GaN substrate), a step of grinding/polishing the gallium nitride substrate, a step of boiling and cleaning the gallium nitride substrate at a predetermined temperature and a step of wet-etching the gallium nitride substrate at a predetermined temperature. In the present embodiment, the GaN substrate is formed by the VAS method.

Firstly, a GaN base layer is grown on a sapphire substrate by a MOVPE method. A metal Ti thin film is deposited on the GaN base layer. Subsequently, by heat treatment in a mixture stream of ammonium and hydrogen gas, the metal Ti thin film is nitride to turn into a TiN thin film having a mesh structure and also the GaN base layer is etched to form voids thereon, thereby forming a void-containing substrate.

Figure 3:
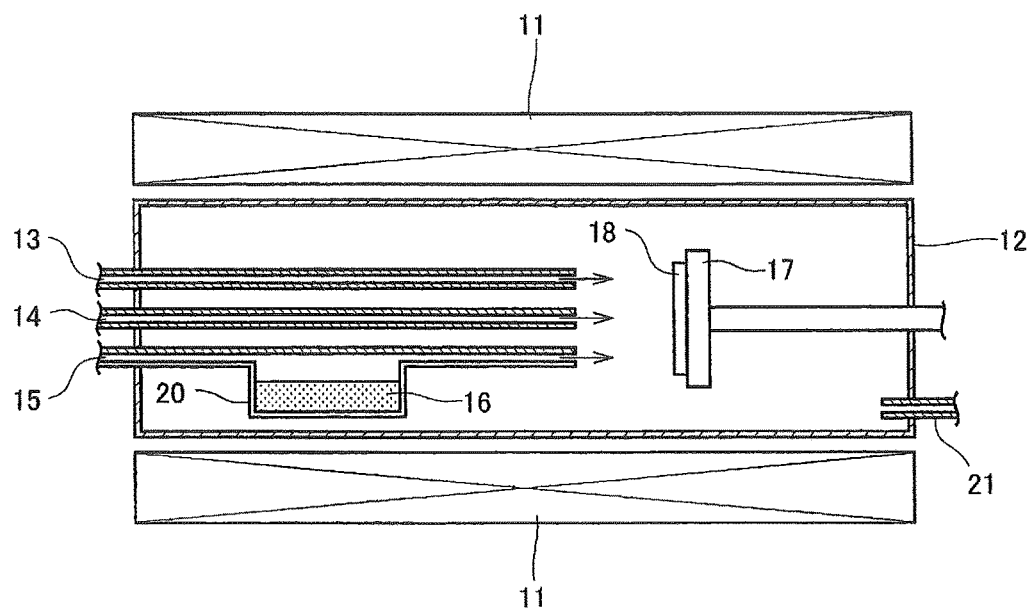
FIG. 3 is a schematic cross sectional view showing an HVPE apparatus for manufacturing a gallium nitride substrate in an embodiment of the present invention.

Following this, a GaN crystal is grown on the void-containing substrate by the hydride vapor phase epitaxy (HVPE) method using GaCl and $NH_3$ as raw materials. In the HVPE method, a crystal growth rate is high and it is possible to easily grow a thick GaN crystal film. For growing a crystal by the HVPE method, an HVPE apparatus as shown in FIG. 3 is used.

The HVPE apparatus has a reaction tube 12 and a heater 11 provided therearound. The reaction tube 12 has a substrate holder 17 for placing a void-containing substrate 18, reaction gas inlet tubes 13 and 15 opening near the void-containing substrate 18, an etching gas inlet tube 14 opening near the void-containing substrate 18 and an exhaust outlet 21. A raw material deposition chamber 20 having a Ga metal 16 therein is provided on the reaction gas inlet tube 15.

$NH_3$ is supplied to the reaction gas inlet tube 13 and HCl gas is supplied to the reaction gas inlet tube 15. The reaction gases are supplied together with a carrier gas such as $H_2$ or $N_2$. In the reaction gas inlet tube 15, the Ga metal 16 housed in the raw material deposition chamber 20 is reacted with HCl and GaCl is thereby produced. In other words, GaCl and $NH_3$ are supplied from the reaction gas inlet tubes 13 and 15 to the void-containing substrate 18. GaCl is reacted with $NH_3$ and a GaN crystal is thereby vapor-grown on the void-containing substrate 18. The HCl gas for etching is supplied from the etching gas inlet tube 14 to the void-containing substrate 18. The HCl gas is supplied continuously during a crystal growth process or is supplied between crystal growth processes in order to make individual initial nuclei large.

The thick GaN film is naturally separated from the sapphire substrate at the voids in the course of temperature drop after the crystal growth and the GaN substrate (GaN free-standing substrate) is thereby obtained.

Subsequently, the GaN substrate is attached and fixed to a ceramic plate by a wax and the back surface of the GaN substrate is ground/polished to improve flatness of the GaN substrate. Likewise, the front surface (growth face) of the GaN substrate is ground/polished. Diamond slurry which is abrasive grain is embedded into the surface of the GaN substrate in this process. Meanwhile, the wax is removed by heating but slightly remains on the surface of the substrate. In other words, a carbon component is attached to and remains on the surface of the GaN substrate in the grinding/polishing process.

Following this, the polished GaN substrate is boiled and cleaned at a predetermined temperature. The residual wax on the surface of the GaN substrate is removed by this cleaning process, thereby reducing the carbon component on the substrate surface. Temperature for boiling and cleaning is preferably not less than 40° C. By setting the temperature to not less than 40° C., reactivity of a cleaning agent used is improved and it is possible to dissolve the wax containing the carbon component and thus to enhance removal thereof. In other words, it is possible to appropriately remove the carbon component and thus to increase the $GaL\alpha/CK\alpha$ peak intensity ratio in the EDX spectrum. The cleaning agent to be used is not specifically limited but is preferably isopropyl alcohol (IPA) which can appropriately remove the carbon component derived from the wax.

Furthermore, the polished GaN substrate is wet-etched at a predetermined temperature. Processing strain on the GaN substrate is removed by the wet-etching process. In addition, the residual wax which could not be completely removed in the cleaning process is removed, together with the diamond slurry embedded into the surface of the GaN substrate, by the wet-etching process, thereby reducing the amount of residual carbon on the substrate surface. In the etching process, the etching is preferably carried out at not less than 77° C. by heating etchant. Etching at a relatively high temperature improves etching reactivity and thus allows etching treatment time to be shortened. In addition, it is possible to dissolve the wax and thus to appropriately remove the carbon component.

Method of Manufacturing Optical Device

Next, a method of manufacturing an optical device in which the GaN substrate obtained as described above is used to manufacture the optical device will be described.

A nitride semiconductor crystal such as InGaN is epitaxially grown on the surface of the above GaN substrate by the MOVPE method. In the present embodiment, since the amount of the residual carbon component on the surface of the GaN substrate is small, crystal quality of the nitride semiconductor crystal to be grown is good. In addition, good crystal quality provides high emission intensity, reduces failures caused by a decrease in emission intensity and allows a yield to be improved.

Although the gallium nitride substrate formed by the VAS method has been described in the embodiment, the invention is not limited thereto and is applicable to a gallium nitride substrate formed by the DEEP method, etc., in the same manner.

EXAMPLES

Gallium nitrides substrate and optical devices in Examples of the invention were manufactured by the following method under the following conditions. These Examples are the illustrative gallium nitride substrate and optical device of the invention and the invention is not limited to these Examples.

Example 1

In Example 1, a GaN single crystal was grown by the VAS method to make a GaN substrate.

Firstly, a void-containing substrate was prepared. For making the void-containing substrate, a 500 nm-thick GaN base layer was formed on a sapphire substrate (3.5 inches in diameter) by the MOVPE method, etc., a 30 nm-thick Ti layer was deposited on a surface thereof, and subsequently, heat treatment (at a temperature of 1000° C.) was carried out in a mixture gas of $H_2$ and $NH_3$ for 30 minutes to form voids in the GaN layer while converting the Ti layer into TiN having a mesh structure.

The void-containing substrate was placed on the substrate holder 17 in the HVPE apparatus shown in FIG. 3, and was heated in the reaction tube 12 at atmospheric pressure so as to have a substrate temperature of 1050° C. The initial nucleation conditions were as follows: $5 \times 10^{-2}$ atm of $NH_3$ gas was introduced together with $6 \times 10^{-1}$ atm of $N_2$ gas as a carrier gas from the reaction gas inlet tube 13, $5 \times 10^{-3}$ atm of GaCl gas was introduced together with $2.0 \times 10^{-1}$ atm of $N_2$ gas and $1.0 \times 10^{-1}$ atm of $H_2$ gas as carrier gases from the reaction gas inlet tube 15 and a crystal was grown for 20 minutes.

After the initial nucleation, the crystal was grown under the same conditions as the initial nucleation conditions except that the partial pressure of GaCl gas was set to be $1.5 \times 10^{-2}$ atm and the partial pressure of $N_2$ gas as the carrier gas of $NH_3$ gas was set to be $5.85 \times 10^{-1}$ atm. The crystal was then grown until the entire GaN crystal becomes 900 μm, thereby obtaining the GaN crystal. The thick GaN film was naturally separated from the sapphire substrate in the course of temperature drop after the growth of the GaN crystal, thereby obtaining a free-standing GaN substrate.

Subsequently, the surface of the GaN substrate was attached and fixed to a ceramic plate using a wax. After that, the back surface of the GaN substrate was ground by a horizontal surface grinding machine. The conditions for grinding the back surface were as follows: grinding stone used—metal bond #800; diameter of grinding stone—150 mm; rotation speed of grinding stone—2000 rpm; feeding speed of grinding stone—0.1 μm/second; and grinding time—30 minutes. Furthermore, the back surface of the GaN substrate was polished by a high speed single-surface precision lapping machine. The conditions for mechanical polishing of N-polar surface were as follows: rotation speed of surface plate—200 rpm; pressure—0.25 MPa; polishing solution—diamond slurry (loose abrasive) having a grain diameter of 3 μm; feed rate of polishing solution—0.3 L/min; and polishing time—20 minutes. Then, the ceramic plate to which the GaN substrate is attached was heated by a hot plate to melt the wax, thereby separating the GaN substrate.

In addition, the front surface which is another surface of the GaN substrate was ground/polished in the same manner as the back surface. The grinding conditions were as follows: grinding stone used—metal bond #800; diameter of grinding stone—200 mm; rotation speed of grinding stone—2500 rpm; feeding speed of grinding stone—0.1 μm/second; and grinding time—30 minutes. The polishing conditions were as follows: rotation speed of surface plate—200 rpm; pressure—0.30 MPa; polishing solution—diamond slurry (loose abrasive) having a grain diameter of 1 μm; feed rate of polishing solution—0.30 L/min; and polishing time—20 minutes. The ground and polished GaN substrate then had a thickness of 400 μm.

Subsequently, the outer diameter process was performed on the GaN substrate by an outer diameter processing machine so as to have a diameter of 76.2 mm (3 inches).

Next, for the purpose of removing the wax attached to the surface of the GaN substrate, the substrate was boiled and cleaned for 30 minutes using IPA (isopropyl alcohol). During the cleaning, the cleaning temperature was set to 41° C. In addition, for the purpose of removing processing strain on the GaN substrate and the carbon component derived from the diamond slurry embedded into the substrate surface, wet-etching was carried out by immersing the GaN substrate in a 25% $NH_4OH$ solution. The wet-etching was carried out for 90 minutes at an etching temperature of 77° C. The cleaning condition and the wet-etching condition of the GaN substrate are shown in Table 1.

TABLE 1

|  | IPA boiling-cleaning temperature | Wet-etching temperature |
|---|---|---|
| Example 1 | 41 | 77 |
| Example 2 | 44 | 78 |
| Example 3 | 47 | 79 |
| Example 4 | 50 | 80 |
| Example 5 | 53 | 81 |
| Example 6 | 56 | 82 |
| Example 7 | 59 | 83 |
| Example 8 | 62 | 84 |
| Example 9 | 65 | 85 |
| Example 10 | 68 | 86 |
| Example 11 | 71 | 87 |
| Example 12 | 74 | 88 |
| Example 13 | 77 | 89 |
| Example 14 | 80 | 90 |
| Comparative Example 1 | 20 | 70 |
| Comparative Example 2 | 23 | 71 |
| Comparative Example 3 | 26 | 72 |
| Comparative Example 4 | 29 | 73 |
| Comparative Example 5 | 32 | 74 |
| Comparative Example 6 | 35 | 75 |
| Comparative Example 7 | 38 | 76 |

Lastly, the GaN substrate was washed with pure water and was dried by a nitrogen gun, thereby obtaining a GaN substrate of Example 1.

Examples 2 to 14 and Comparative Examples 1 to 7

GaN substrates in Examples 2 to 14 and Comparative Examples 1 to 7 were made under the same conditions as Example 1 except that the cleaning condition (cleaning temperature) and the wet-etching condition (etching temperature) of Example 1 were changed to those shown in Table 1.

EDX measurement was performed on the surfaces of the GaN substrates obtained in Examples 1 to 14 and Comparative Examples 1 to 7, and the amount of residual carbon on the surface of the GaN substrate was each evaluated. In detail, using VE-9800S (manufactured by KEYENCE CORPORATION) as a scanning electron microscope (SEM) and GENESIS2000 (manufactured by EDAX Inc.) as an EDX spectrum detector, EDX spectrum at the center of the GaN substrate was measured at a characteristic x-ray takeoff angle of 16.28°. The measurement was performed while changing the accelerating voltage of the SEM from 3 kV, 5 kV to 8 kV. The electron penetration depths at respective accelerating voltages calculated from the formula (1) are respectively 0.09 μm, 0.20 μm and 0.45 μm. Then, in order to measure the amount of carbon near the surface of the GaN substrate, a ratio of GaLα peak intensity (about 1.100 keV) to CKα peak intensity (about 0.266 keV) in EDX spectrum was examined. The results thereof are shown in Table 2.

TABLE 2

| | GaLα/CKα in EDX spectrum | | |
|---|---|---|---|
| | Accelerating voltage 3 kV | Accelerating voltage 5 kV | Accelerating voltage 8 kV |
| Example 1 | 2.0 | 31.1 | 41.3 |
| Example 2 | 2.2 | 32.7 | 40.6 |
| Example 3 | 2.4 | 31.7 | 39.7 |
| Example 4 | 2.6 | 33.7 | 42.9 |
| Example 5 | 2.8 | 32.4 | 38.1 |
| Example 6 | 3.0 | 33.8 | 39.0 |
| Example 7 | 4.3 | 32.7 | 41.5 |
| Example 8 | 5.4 | 31.5 | 38.6 |

TABLE 2-continued

GaLα/CKα in EDX spectrum

| | Accelerating voltage 3 kV | Accelerating voltage 5 kV | Accelerating voltage 8 kV |
|---|---|---|---|
| Example 9 | 7.0 | 33.6 | 39.0 |
| Example 10 | 8.9 | 32.9 | 41.1 |
| Example 11 | 10.3 | 31.9 | 40.6 |
| Example 12 | 11.5 | 32.8 | 39.9 |
| Example 13 | 12.9 | 31.9 | 39.2 |
| Example 14 | 14.1 | 32.8 | 40.1 |
| Comparative Example 1 | 0.8 | 33.2 | 39.7 |
| Comparative Example 2 | 0.9 | 31.0 | 42.5 |
| Comparative Example 3 | 1.1 | 31.8 | 41.6 |
| Comparative Example 4 | 1.3 | 32.0 | 38.4 |
| Comparative Example 5 | 1.5 | 32.5 | 40.6 |
| Comparative Example 6 | 1.7 | 31.4 | 42.8 |
| Comparative Example 7 | 1.9 | 33.7 | 38.5 |

From Table 2, it was confirmed that, when the accelerating voltage of the SEM is 3 kV, the GaLα/CKα peak intensity ratio increases with an increase in the IPA boiling-cleaning temperature and NH$_4$OH wet-etching temperature and carbon near the substrate surface is removed. On the other hand, when the accelerating voltage of the SEM was 5 kV and 8 kV, the GaLα/CKα peak intensity ratio in the EDX spectrum hardly changed. This is because the penetration depth of electron beam into the surface of the GaN substrate is too far and variation in carbon level near the substrate surface is not observed. Therefore, an appropriate accelerating voltage is considered to be 3 kV in order to examine the variation in carbon level near the surface.

Following this, optical devices were manufactured using the GaN substrates obtained in Examples and Comparative Examples, and crystal quality was evaluated by measuring emission intensity thereof.

Figure 4:
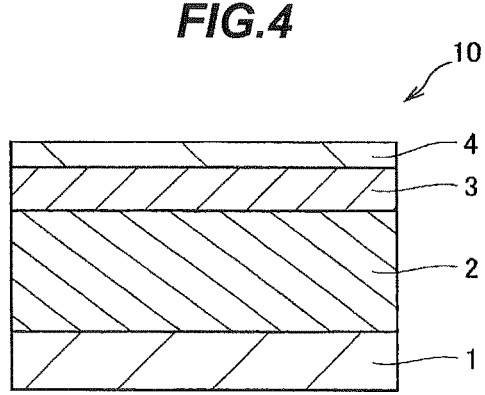
FIG. 4 is a schematic cross sectional view showing an optical device in the embodiment of the invention.

A H$_2$ carrier gas, ammonium, trimethylgallium and trimethylindium were supplied onto a Ga-polar surface (front surface) of the GaN substrate at a substrate temperature of 1020° C. by the MOVPE method, thereby growing a structure of the epitaxial film shown in FIG. 4. In detail, a GaN buffer layer 2 (2500 nm in thickness), an InGaN barrier layer (about 8 nm in thickness) and an InGaN well layer (about 5 nm in thickness) were alternately laminated six times on the GaN substrate 1 (400 μm in thickness) of Example 1, and a multiple quantum well layer 3 formed by growing the InGaN barrier layer (about 8 nm in thickness) and a GaN cap layer 4 (about 30 nm in thickness) were further laminated thereon, thereby making an optical device 10.

Photoluminescence peak intensity corresponding to a band gap of an InGaN quantum well layer at the center of the GaN substrate was measured on the obtained optical device by a photoluminescence measurement system RPM 2000 (manufactured by Accent). The photoluminescence measurement conditions were as follows: laser light source—He—Cd laser with a wavelength of 325 nm; width of light receiving slit—0.1 mm; and measurement-wavelength range—367.9 nm to 432.4 nm. Emission intensity of the GaN substrate was examined. The examination results are shown in Table 3.

TABLE 3

| | Photoluminescence emission intensity |
|---|---|
| Example 1 | 1.515 |
| Example 2 | 1.547 |
| Example 3 | 1.493 |
| Example 4 | 1.525 |
| Example 5 | 1.563 |
| Example 6 | 3.152 |
| Example 7 | 3.045 |
| Example 8 | 2.997 |
| Example 9 | 3.078 |
| Example 10 | 2.965 |
| Example 11 | 3.036 |
| Example 12 | 3.058 |
| Example 13 | 2.987 |
| Example 14 | 3.015 |
| Comparative Example 1 | 0.543 |
| Comparative Example 2 | 0.589 |
| Comparative Example 3 | 0.478 |
| Comparative Example 4 | 0.552 |
| Comparative Example 5 | 0.513 |
| Comparative Example 6 | 0.492 |
| Comparative Example 7 | 0.524 |

According to Table 3, in the optical devices of Examples 1 to 5 in which a peak intensity ratio is not less than 2 and less than 3, the photoluminescence emission intensity is 1.493 to 1.563 Volt/mW. In addition, in the optical devices of Examples 6 to 14 in which a peak intensity ratio is not less than 3, the emission intensity is 2.965 to 3.152 Volt/mW. On the other hand, in the optical devices of Comparative Examples 1 to 7 in which a peak intensity ratio is less than 2, the emission intensity is 0.478 to 0.589 Volt/mW. In other words, emission intensity is lower in Comparative Examples 1 to 7 than in Examples 1 to 14.

In Comparative Examples 1 to 7, the GaN substrate, of which GaLα/CKα peak intensity ratio at an accelerating voltage of 3 kV is less than 2 and in which the amount of residual carbon on the surface is large, is used and it is thus considered that the crystal quality deteriorates at the time of growing the nitride semiconductor crystal and emission intensity decreases. In contrast, the GaN substrate in which the peak intensity ratio is not less than 2.0 is used in Examples 1 to 14 and it is thus considered that the amount of residual carbon component on the surface is small and the crystal quality of the nitride semiconductor crystal to be grown is good. Especially in Examples 6 to 14 in which the peak intensity ratio is not less than 3.0, the amount of residual carbon is smaller and it is thus considered that the crystal quality of the epitaxial growth layer is better. As a result of having good crystal quality, a decrease in emission intensity was suppressed in the optical devices of Examples 1 to 14, thereby obtaining large emission intensity.

Although the invention has been described with respect to the specific embodiment for complete and clear disclosure, the appended claims are not to be therefore limited but are to be construed as embodying all modifications and alternative constructions that may occur to one skilled in the art which fairly fall within the basic teaching herein set forth.

The invention claimed is:

1. A method of making a gallium nitride substrate, comprising:
providing a gallium nitride substrate; and
measuring a GaLα/CKα peak intensity ratio in energy dispersive X-ray microanalysis (EDX) spectrum of a surface of the gallium nitride substrate, the EDX spectrum being obtained in an EDX of the surface of the gallium nitride substrate using a scanning electron microscope (SEM) at an accelerating voltage of 3 kV.

2. The method of claim 1, wherein the measured GaLα/CKα peak intensity ratio in the EDX spectrum of the surface of the gallium nitride substrate is not less than 2.

3. The method of claim 1, further comprising:
polishing a surface of the gallium nitride substrate, and
wherein the measuring of the GaLα/CKα peak intensity ratio comprises measuring the GaLα/CKα peak intensity ratio of the polished surface.

4. The method of claim 3, further comprising:
after the polishing of the surface of the gallium nitride substrate, cleaning the polished surface of the gallium nitride substrate,
wherein the measuring of the GaLα/CKα peak intensity ratio is performed after the cleaning of the surface of the gallium nitride substrate.

* * * * *